United States Patent [19]

Ryder

[11] 4,208,583
[45] Jun. 17, 1980

[54] DETECTION OF ANALYSIS OF PARTICULATE MATERIAL IN FLUID STREAMS

[75] Inventor: Dennis M. Ryder, Northumberland, England

[73] Assignee: Reyrolle Parsons Limited, England

[21] Appl. No.: 907,767

[22] Filed: May 19, 1978

[30] Foreign Application Priority Data

May 19, 1977 [GB] United Kingdom .............. 21095/77

[51] Int. Cl.² .......................... G09K 3/00; G01J 1/42
[52] U.S. Cl. .................................. 250/302; 250/364; 250/365; 250/564; 250/574
[58] Field of Search .............. 250/302, 365, 373, 364, 250/564, 574

[56] References Cited

U.S. PATENT DOCUMENTS

| | | |
|---|---|---|
| 2,096,099 | 10/1937 | Gaugler .............................. 250/302 |
| 3,457,407 | 7/1969 | Goldberg ............................ 250/373 |
| 3,697,226 | 10/1972 | Hirschfeld et al. .................. 250/365 |
| 3,710,111 | 1/1973 | Collura ................................ 250/373 |
| 3,826,920 | 7/1974 | Woodroffe ......................... 250/373 |

*Primary Examiner*—Harold A. Dixon
*Attorney, Agent, or Firm*—Holman & Stern

[57] ABSTRACT

Apparatus for the detection and analysis of particulate material carried in a fluid stream comprising a sampling device through which the fluid stream may be passed, said sampling device incorporating means for arresting and carrying an accumulation of particles restrained from flow in the fluid stream, means for directing ultra-violet radiation onto the sampling device at a location where the accumulation of particles results, and means whereby optical radiation analysis may be performed of the radiation emitted by the accumulation of particles consequent upon their excitation by the ultra-violet radiation means.

1 Claim, 1 Drawing Figure

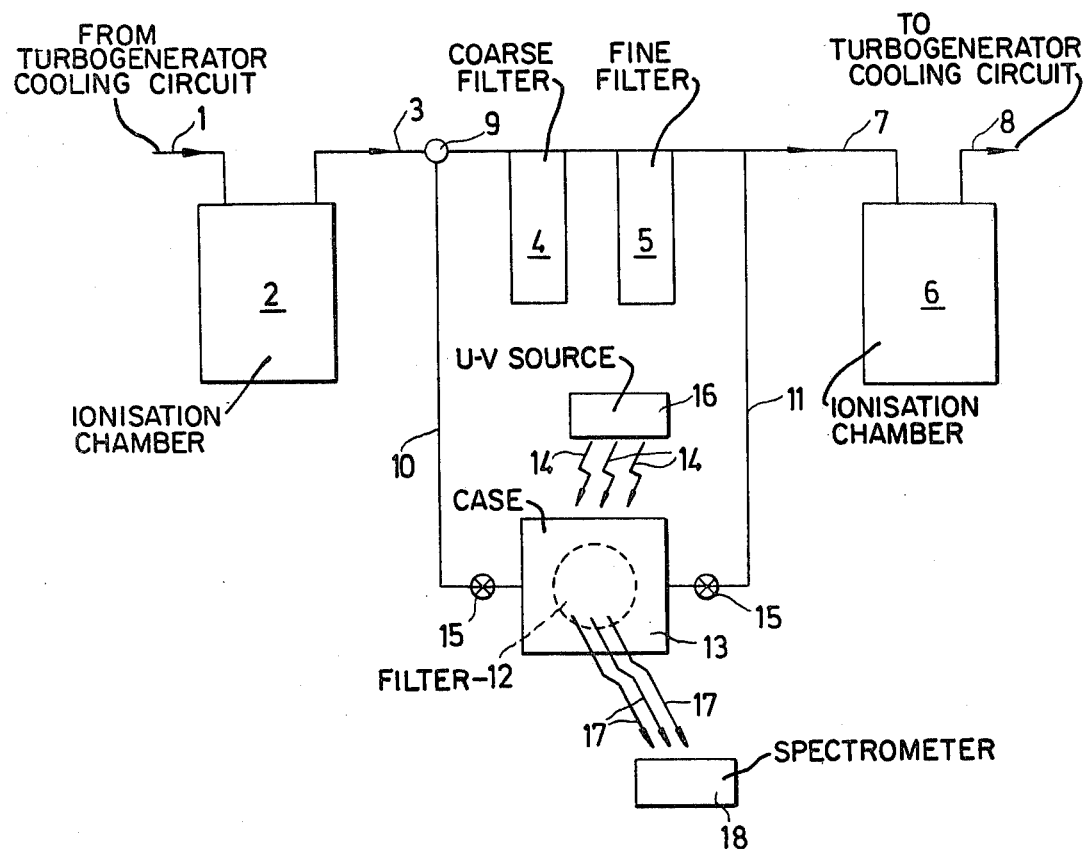

DETECTION OF ANALYSIS OF PARTICULATE MATERIAL IN FLUID STREAMS

This invention relates to apparatus and method for the detection and analysis of particulate matter in gas streams.

It is known that when overheating occurs in the core and conductors of a dynamo-electric machine as a result of high flux densities in the laminations, the overheating causes decomposition of the individual coatings of insulation material on the laminations and consequently sub-micron particles of organic material are released.

It has been proposed to detect the onset of overheating at an early stage by extracting part of the cooling gas from a large hydrogen-cooled dynamo-electric machine while it is in operation and circulating the extracted gas through an ion particle detection chamber in order to detect the presence of sub-micron particles resulting from overheating. Such a system, whilst lending itself to continuous monitoring systems for a dynamo-electric machine, does not discriminate between detected particles of different constitution. In some instances this could lead to a machine being shut down due to suspected insulation overheating when the particles may prove to stem from, for example, oil at a faulty hydrogen oil seal, which latter condition could be rectified without reducing the machine loading.

Accordingly, the object of the present invention is to provide apparatus analytically responsive to particulate organic material of differing chemical constitutions carried in a gas stream.

A further object of the invention is to provide overheating detection apparatus for a gas-cooled machine provided with a facility whereby the nature of differing particles in the gas coolant may be distinguished.

The invention consists in apparatus for the detection and analysis of particulate material carried in a fluid stream comprising a sampling device through which the fluid stream may be passed, said sampling device incorporating means for arresting and carrying an accumulation of particles restrained from flow in the fluid stream, means for directing ultra-violet radiation onto the sampling device at a location where the accumulation of particles results, and means whereby optical radiation analysis may be performed of the radiation emitted by the accumulation of particles consequent upon their excitation by the ultra-violet radiation means.

The means for arresting and carrying the accumulation of particles preferably comprises a filter for filtering a fluid medium.

The invention further consists in a method for the detection and analysis of particulate material carried in a fluid stream comprising passing a fluid stream through a sampling device, arresting and carrying by means of said sampling device an accumulation of particles restrained from flow in the fluid stream, directing ultra-violet radiation onto the sampling device at a location where the accumulation of particles results, and performing optical radiation onto the sampling device at a location where the accumulation of particles results, and performing optical radiation analysis of the radiation emitted by the accumulation of particles consequent upon their excitation by the ultra-violet radiation.

The radiation emitted by the accumulation of particles is fluorescent radiation caused by the ultra-violet light excitation, and in the simplest case may be examined for colour by a human observer, variations of colour due to particles of differing chemical constitution being assessed. Preferably, however, spectrographic or other analysis equipment is used to ascertain the nature of the particles detected and, in a monitoring system for a gas cooled turbogenerator, for example, the result of the analysis may be arranged to effect emergency measures automatically only when such measures are dictated as being necessary according to the presence of particles of a particular nature to a particular quantitative level.

The invention will now be further described in the form of its preferred embodiments and with reference to the accompanying drawing which shows a schematic flow-line arrangement for apparatus according to the invention used in a turbogenerator cooling gas monitoring system.

Referring to the aforesaid drawing, hydrogen gas coolant from the cooling circuit of a turbogenerator (not shown) is fed by a line 1 into an ionisation chamber 2, and thence by way of a line 3 to a dual filter arrangement comprising a coarse filter 4 and a fine filter 5. The coolant then passes to an ionisation chamber 6 via a line 7 and is finally returned to the cooling circuit by a line 8.

Filters 4 and 5 are arranged to be by-passed by a twoway valve 9 and lines 10 and 11 leading respectively to and from a filter 12 housed in a transparent or part-transparent case 13. A microporous filter, for example a poly-tetrafluoro-ethylene diaphragm filter, is the preferred form of filter 12. The surface of filter 12, which is visible through case 13, is illuminated by ultra-violet radiation indicated by arrows 14, from a suitable source 16. Filter 12 and case 13 may be isolated by means of valves 15 in lines 10 and 11.

Detection of organic particles in the coolant gas stream may be achieved by passage of the gas through filters 4 and 5 only, independently of the apparatus of the present invention. This involves taking electrical outputs from the ionisation chambers 2 and 6 and applying them to a differential amplifier (not shown), which gives a positive indication of the presence of particles in the gas stream when the particle flow through chamber 2 is greater than that through chamber 6 due to the collection of particles by filters 4 and 5.

In order to determine whether the particles detected in accordance with the preceding paragraph are of such a nature as to cause concern for the continued running of the alternator, valve 9 may be switched to cause the coolant gas to flow through the filter 12 provided in accordance with the present invention. Alternatively, filter 12 may be maintained in circuit continuously. This filter collects the contamination from the coolant which is then irradiated by the ultra-violet source. The visible fluorescence spectrum emitted as at 17 may then be examined and quantified.

The origin of the contamination causing initial differential response to the ionisation chambers 2 and 6, that is to say, whether the response is due to other than over-heating problems such as oil or water vapour, for which no emergency action need necessarily be taken, or whether it is due to excessive heating or organic insulants necessitating reduced loading of the machine during which further examination of the machine may be made, is determinable from the fluorescence spectrum obtained as described. Emergency shut-down would be effected only in extreme cases. Particles due to oil, for example, fluoresce very brightly, whilst particles due to overheating of various insulation materials are identifiable by the differing wavelength/intensity characteristics determinable by, for example, a linear grating spectrometer 18. The latter information is useful to indicate what further analytic techniques may be most useful, for example, infra-red spectrography, gas chromatography, mass spectrometry or chemical analysis. Samples of the contaminating material may readily be removed from the apparatus for the purpose of such further analysis whilst a machine is running without interrupting the continuous monitoring facility.

Identification of the particular material located at the "hot spot" of a faulty machine may be made at an early stage in the development of the fault by the apparatus according to the invention.

The invention is not limited solely to the detection and analysis of organic materials, nor to the application of the apparatus to gas monitoring, since particles in liquid streams can also be examined by the techniques afforded by the apparatus.

It should be further noted that it is not essential that apparatus according to the invention should operate in conjunction with ionisation detection techniques.

We claim:

1. An apparatus for the detection analysis of particulate material carried in a fluid cooling stream of a dynamo-electric machine, comprising:
    an at least partially transparent sampling means through which the fluid cooling stream may be passed;
    said sampling means incorporating removable filter means for arresting an accumulation of particles restrained from flow in the fluid stream;
    means for directing ultra-violet radiation onto said removable filter means at a location where the accumulation of particles results; and
    spectrometer means whereby optical radiation analysis may be performed on radiation emitted by the accumulation of particles cconsequent upon their excitation by the ultra-violet radiation means.

* * * * *